US012083250B2

(12) United States Patent
Van Weerd (10) Patent No.: US 12,083,250 B2
(45) Date of Patent: Sep. 10, 2024

(54) UNIVERSAL METHOD FOR THE PREPARATION OF LIPID-BASED COATINGS

(71) Applicant: LIPOCOAT B.V., Enschede (NL)

(72) Inventor: Jasper Van Weerd, Enschede (NL)

(73) Assignee: LIPOCOAT IP HOLDING B.V., Enschede (NL)

( * ) Notice: Subject to any disclaimer, the term of this patent is extended or adjusted under 35 U.S.C. 154(b) by 1050 days.

(21) Appl. No.: 16/975,842

(22) PCT Filed: Feb. 26, 2019

(86) PCT No.: PCT/EP2019/054698
§ 371 (c)(1),
(2) Date: Aug. 26, 2020

(87) PCT Pub. No.: WO2019/166416
PCT Pub. Date: Sep. 6, 2019

(65) Prior Publication Data
US 2020/0405919 A1 Dec. 31, 2020

(30) Foreign Application Priority Data

Feb. 27, 2018 (EP) ..................................... 18158839

(51) Int. Cl.
| | |
|---|---|
| *A61L 29/16* | (2006.01) |
| *A61L 29/08* | (2006.01) |
| *A61L 31/08* | (2006.01) |
| *A61L 31/16* | (2006.01) |
| *G02B 1/10* | (2015.01) |

(52) U.S. Cl.
CPC ............... *A61L 29/16* (2013.01); *A61L 29/08* (2013.01); *A61L 31/08* (2013.01); *A61L 31/16* (2013.01); *G02B 1/10* (2013.01); *A61L 2300/22* (2013.01); *A61L 2300/606* (2013.01); *A61L 2300/62* (2013.01)

(58) Field of Classification Search
CPC .......... A61L 29/16; A61L 29/08; A61L 31/08; A61L 31/16; G02B 1/10
See application file for complete search history.

(56) References Cited

U.S. PATENT DOCUMENTS

| | | | |
|---|---|---|---|
| 2008/0241942 A1 | 10/2008 | Zhu et al. | |
| 2017/0298297 A1 | 10/2017 | Klein et al. | |

FOREIGN PATENT DOCUMENTS

| | | | | |
|---|---|---|---|---|
| EP | 1323415 B1 | * | 1/2010 | ......... A61K 31/7088 |
| EP | 3093661 A1 | | 11/2016 | |
| JP | 201328649 A | | 2/2013 | |
| WO | WO-0158910 A2 | * | 8/2001 | .......... A61K 9/1075 |
| WO | 2014/184383 A1 | | 11/2014 | |
| WO | WO-2015193887 A1 | * | 12/2015 | .......... A61K 31/728 |

OTHER PUBLICATIONS

Zhang, Y. et al., PEGylated Phospholipid Membrane on Polymer Cushion and Its Interaction with Cholesterol, Langmuir, 2010. vol. 26, No. 13, pp. 111410-11144 (Year: 2910).*
Notice of Reasons for Refusal, dated Sep. 20, 2022 for corresponding Japanese Application 2020-567636.
Cruz et al., A Membrane-Translocating Peptide Penetrates into Bilayers without Significant Bilayer Pertubations, Biophysical Journal, Elsevier, Amsterdam, NL, Jun. 2013, vol. 104, No. 11, pp. 2419-2428.
Howell et al., Amitriptyline Overdose Treatment by Pegylated Anionic Liposomes, Journal of Colloid and Interface Science, Academic Press, Inc., US, Aug. 1, 2008, vol. 324, No. 1-2, pp. 61-70.
Van Weerd, J., Novel Biomedical Applications of Supported Lipid Bilayers, PhD Thesis, Jan. 16, 2015.
Chinese Office Action dated Feb. 4, 2023 for family member Application No. 201980015651.9.
Jasper Van Weerd, Novel Biomedical Applications of Supported Lipid Bilayers, PhD Thesis, Jan. 16, 2015, 194 pages, Nanonextnl, Enschede, the Netherlands.
Pharmaceutics 7th Edition, Cui Fude, Dec. 2011, pp. 407-409, People's Medical Publishing House.

* cited by examiner

*Primary Examiner* — Genevieve S Alley
(74) *Attorney, Agent, or Firm* — Hudak, Shunk & Farine Co. LPA (57) ABSTRACT

A process for making lipid-coated substrates including the steps of a. providing a lipid solution (A) of phospholipids in a water miscible organic solvent at a phospholipid concentration between 25 and 450 mg/ml; b. provide an aqueous solution (B) having pH between 4 and 8; c. agitate the aqueous solution (B) and dispense the lipid solution (A) into the aqueous solution (B) to prepare an aqueous dispersion including lipid vesicles (C) having a number average size between 80 and 120 nm (measured according to dynamic light scattering) at a phospholipid concentration between 0.05 mg/ml and 2 mg/ml; and d. applying the aqueous dispersion (C) to a substrate and formation of a lipid-based coating; wherein aqueous dispersion (C) contains at least 95 wt. % water. Medical devices including a lipid-based coating, for example contact lenses and catheters.

23 Claims, 4 Drawing Sheets

UNIVERSAL METHOD FOR THE PREPARATION OF LIPID-BASED COATINGS

FIELD OF THE INVENTION

The present invention relates to an easy-to-use method to prepare lipid-based coatings on substrates.

BACKGROUND OF THE INVENTION

Coating of substrates is known in the art. In general, coatings are coverings that can be applied to a substrate. Coatings can be for example decorative, functional or both. Decorative coatings include example paints and or lacquers. Functional coatings include for example adhesive, optical, catalytic, light sensitive, magnetic, electrical, conductive, insulating, scent properties and or protective. Functional (protective) coatings include for example anti-corrosion, anti-scratch, waterproof, anti-microbial, anti-inflammatory, anti-fouling, lubricious, hydrophobic, hydrophillic and or bio-active.

Coatings can be applied using for example vapor deposition, chemical and electrochemical techniques, spraying, roll-to-roll coating processes, spin coating and dip coating. Examples of vapor deposition are chemical vapor deposition such as metalorganic vapor phase epitaxy, electrostatic spray assisted vapor deposition (ESAVD) and or sherardizing, physical vapor deposition such as cathodic arc deposition, electron beam physical vapor deposition (EBPVD), ion plating, ion beam assisted deposition (IBAD), magnetron sputtering, pulsed laser deposition, sputter deposition, vacuum deposition, vacuum evaporation, evaporation (deposition). Examples of chemical and electrochemical techniques are conversion coatings such as, anodizing, chromate conversion coating, plasma electrolytic oxidation, phosphate (coating), ion beam mixing, pickled and oiled, electro-less plating and or electroplating. Examples of spraying are spray painting, high velocity oxygen fuel (HVOF), plasma spraying, thermal spraying and or plasma transferred wire arc thermal spraying. Examples of roll-to-roll coating processes are air knife coating, anilox coater, flexo coater, gap coating, gravure coating, hot melt coating, immersion dip coating, kiss coating, metering rod (Meyer bar) coating, roller coating, silk screen coater, slot die coating, inkjet printing, lithography and flexography.

The typical lipid-based coating, not limited to, Supported Lipid Bilayers (SLBs) are commonly applied using vesicles, prepared by sonication or extrusion, of varying size and composition. SLBs are generally prepared via vesicle fusion and have been widely used in research since they were first reported (McConnel and Tamm 1985). SLBs have shown great promise as anti-fouling surface and are tuneable in their surface composition and function. The anti-fouling nature of SLBs and their tuneable composition makes them an ideal candidate to serve as a surface coating on solid materials. However, the use of SLBs in commercial applications has been limited. This is partially due to their lack of stability in air. More recently, methods have been described that enable the formation of air-stable SLBs more suitable for commercial uses.

A method for preparing air-stable SLBs is for example described in US2008/0241942. Here, the bilayer is applied on a solid surface, preferably an array. The method comprises the following steps
    providing a solid surface coated with a molecular film;
    covalently attaching sterol groups to the molecular film and;
    contacting the sterol functionalized molecular film with a lipid solution,
    wherein the lipid solution is prepared via extrusion.

A disadvantage of the method described in US2008/0241942 is that a molecular film, which is for instance a hydrophilic polymer or a hydrogel coating, has to be applied to the solid surface to be able to attach a bilayer. The bilayer is not directly attached to the substrate, but only through the molecular film attached to the solid surface. The molecular film contains reactive groups that will covalently react with sterol groups, that subsequently bind the SLB. This chemical procedure might not be suitable for all materials and give rise to unwanted complications. Moreover, the application of the molecular film on the support is an additional step, which is time consuming and adds to the complexity of the system. Not only the preparation of the SLB needs to be controlled, but also the interaction and adhesion between the substrate and the molecular film, and the stability of the molecular film. Furthermore, the molecular film cannot be applied on all types of solid surfaces. Therefore, limitations exist on the choice of substrate to be used for making a SLB. Another disadvantage is that by the application of the molecular film the chemical and mechanical properties of the solid surface can be changed.

These limitations can be overcome by the use of the method described in WO2014/184383. This method eliminates the need for the molecular film and can be more broadly applied. Here, a method is described for the preparation of a substrate yielding a stable SLB coating comprising the steps of
    providing an object having a surface;
    treating the surface of the object with a plasma containing active oxygen to provide the surface of the object with reactive groups A;
    covalently attaching a sterol group to the reactive groups A, and;
    contacting the object activated with sterol groups with a lipid solution to form a lipid bilayer.

These improvements enable the exploration of lipid coatings for commercial uses. However, the next hurdle is overcoming a major bottleneck in lipid coating preparation namely the preparation of lipid (vesicle) solution. In the above methods or when preparing traditional SLBs, the lipid coating is commonly prepared by means of a lipid vesicle solution that is prepared using the process of extrusion.

For example such extrusion methods are described in Jasper van Weerd: "novel biomedical applications of supported lipid bilayers", PhD Thesis, Jan. 16, 2015 (XP055482572), in WO01/58910, and other documents.

Preparation of lipid vesicle solution using the process of extrusion is time consuming (typically several hours to a day) and is generally done in batches of small quantities.

Preparation of lipid vesicle solution by means of extrusion generally encompass the following steps
    preparation of a dry lipid film in a glass container;
    hydration of the dry lipid film using an aqueous solution;
    optionally sonication and/or freeze-thaw cycles can be employed to aid in hydration;
    and the resulting solution is extruded several times, commonly 11 times or more, through a membrane with well-defined pore sizes to yield the lipid vesicle solution or can be used as such.

SUMMARY OF THE INVENTION

For commercial application of lipid coatings, there is a need for a simpler method to form lipid vesicle solution for the preparation of lipid coatings on substrates that is faster, easier to scale and easier to use.

The present invention relates to a universal method for making lipid-coated substrates comprising the steps of
a) Providing a lipid solution (A) of phospholipids in a water miscible organic solvent at a phospholipid concentration between 25 and 450 mg/ml;
b) Provide an aqueous solution (B) having pH between 4 and 8;
c) Agitate the aqueous solution (B) and dispense the lipid solution (A) into the aqueous solution (B) to prepare an aqueous dispersion comprising lipid vesicles (C) having a number average size between 80 and 120 nm (measured according to dynamic light scattering) at a phospholipid concentration between 0.05 mg/ml and 2 mg/ml; and
d) Applying the aqueous dispersion (C) to a substrate and formation of a lipid-based coating;
wherein aqueous dispersion (C) contains at least 95 wt. % water.

The process of the present invention has the advantage that it is a simple process to form lipid vesicles, it is fast and is compatible for making traditional SLBs and lipid coatings and it is also compatible with different methods for substrate pretreatments such as US2008/0241942 and WO2014/184383. In addition, solutions (A) and (B) can be prepared beforehand as stock solutions to further speed up coating formation to several seconds.

Figure 1:
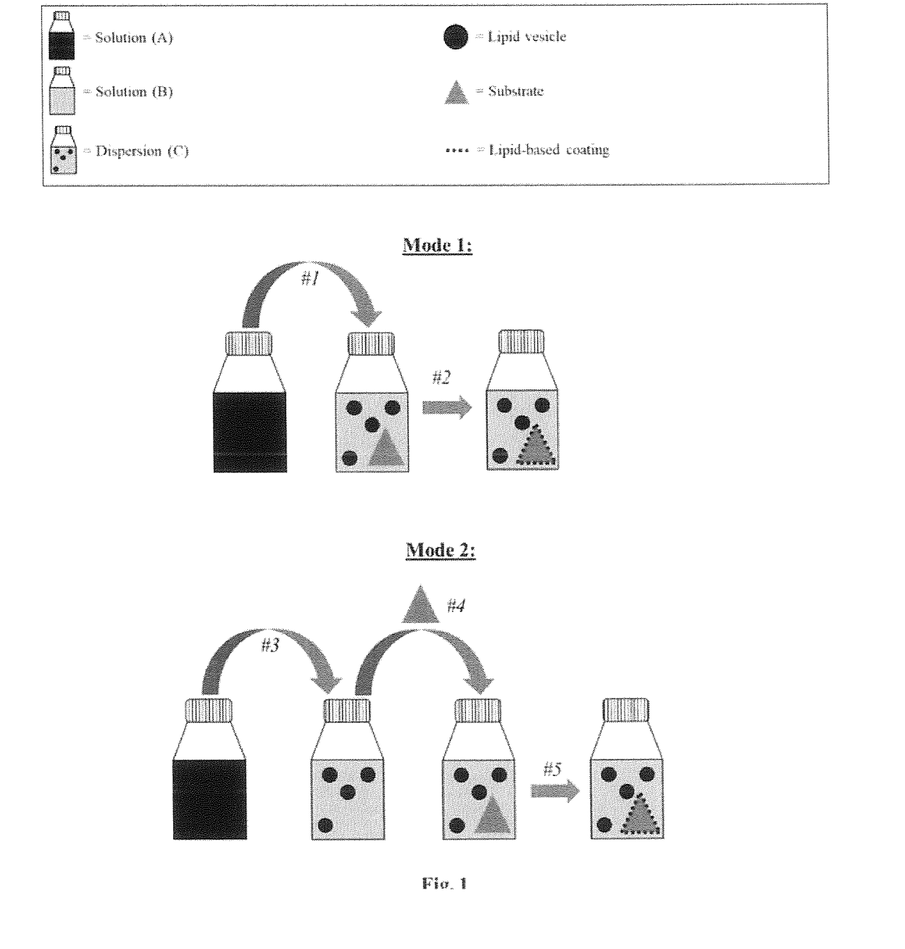
FIG. 1 shows different modes of applying a coating to a substrate: in mode 1 the substrate is present during formation of the dispersion (C), and instantaneous coating of the substrate occurs. In mode 2 first a dispersion (C) is prepared, where after a substrate is added to the dispersion and coating of the substrate takes place.
Figure 2:
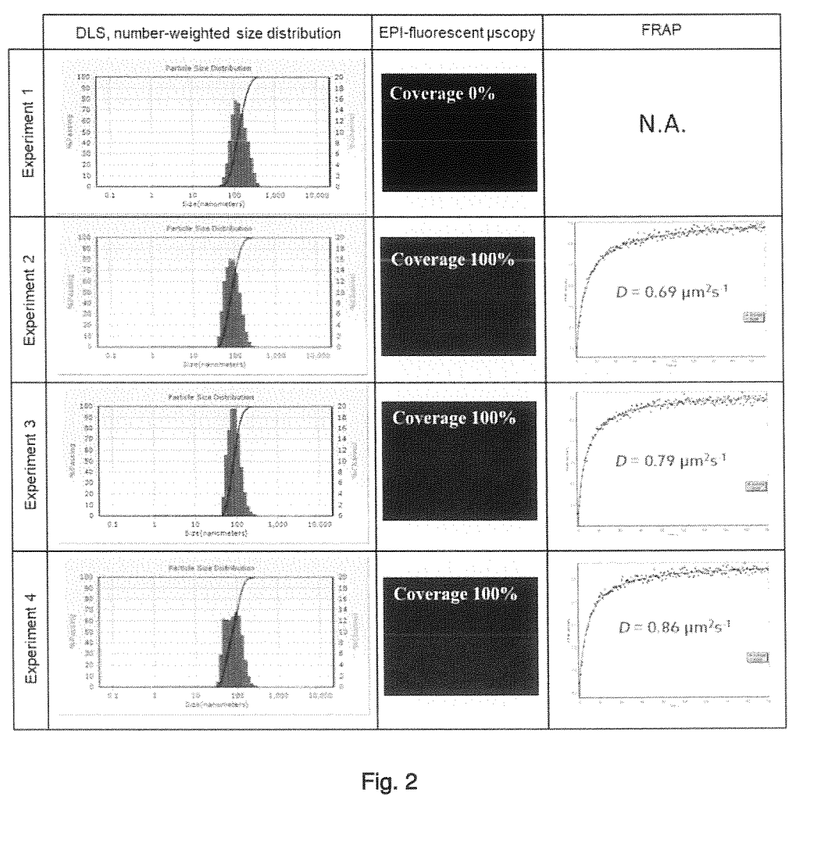
FIG. 2 shows particles size distributions of experiments 1-4.
Figure 3:
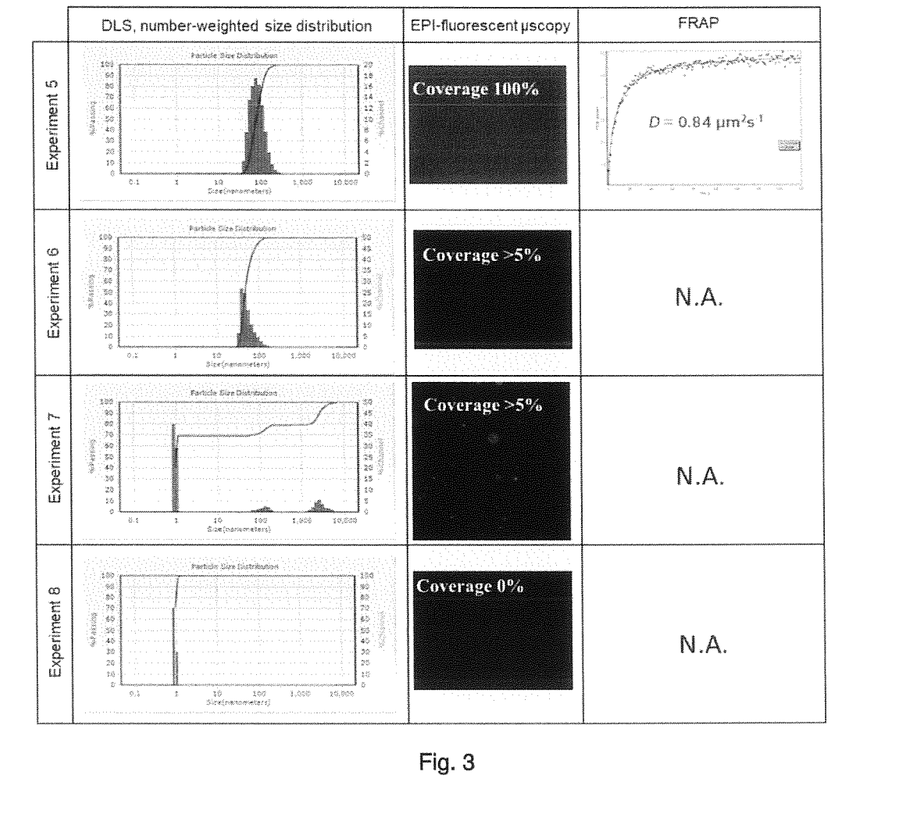
FIG. 3 shows particles size distributions and fluorescence spectra of experiments 5-8
Figure 4:
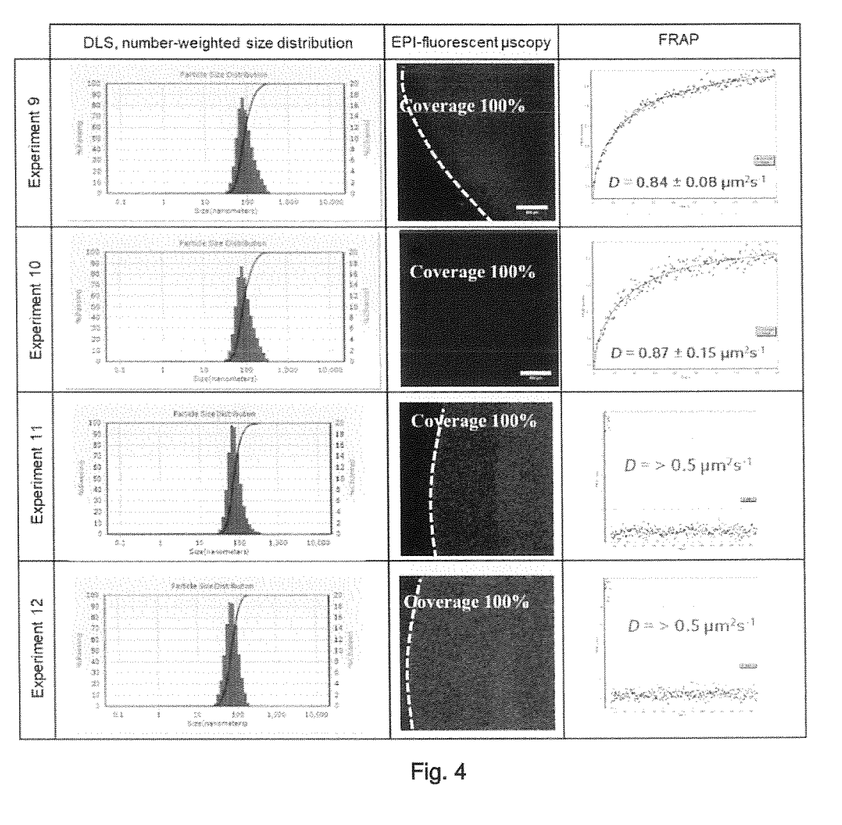
FIG. 4 shows particles size distributions and fluorescence spectra of experiments 9-12.

In a preferred embodiment of the present invention, solution (A) containing a concentrate of phospholipids is prepared in a water-miscible organic solvent and is dispensed into an agitated aqueous solution (B) containing a substrate, resulting in a aqueous dispersion of lipid vesicles (C, FIG. 1—mode 1 #1) and instant fusion of said vesicles into a lipid-based coating on the substrate (FIG. 1—mode 1 #2).

In another embodiment of the present invention, solution (A) containing a concentrate of phospholipids is prepared in a water-miscible organic solvent and is dispensed into an agitated aqueous solution (B), resulting in the formation of vesicles (FIG. 1—mode 2 #3). The resulting aqueous dispersion of lipid vesicles (C), diluted or non-diluted, is brought into contact with a substrate (FIG. 1—mode 2 #4), resulting in instant fusion of vesicles into a lipid-based coating onto the substrate (FIG. 1—mode 2 #5).

DETAILED DESCRIPTION OF THE INVENTION

The invention relates to a universal method for coating of a substrate with a lipid-based coating.

In a first step a solution of phospholipids is prepared in an organic solvent which is readily miscible with water.

Examples of water miscible organic solvents are acetic acid, acetone, acetonitrile, dimethylformamide, dimethyl sulfoxide, dioxane, alcohols, like methanol, ethanol, propanol, glycerol, polyethylene glycol, and tetrahydrofuran.

Examples of preferred suitable organic solvents are methanol, ethanol, propanol, acetone, dimethylformamide, glycerol, polyethylene glycol (PEG), dimethyl sulfoxide and mixtures of these. More preferably the solvent is an alcohol, most preferably the solvent is ethanol.

The temperature of the lipid solution (A) is generally between −20 and 60° C., preferably between 10 and 50° C., most preferably between 15 and 30° C. The temperature should be high enough to obtain a clear solution.

The concentration of phospholipids in solution (A) ranges typically between 25 and 450 mg/ml, preferably between 40 and 200 mg/ml. A concentration of phospholipids of less than 25 mg/ml generally yields a too low concentration of lipid vesicles in dispersion (C), which cannot cover a layer of a substrate effectively. A concentration higher than 500 mg/ml renders lipid vesicles having irregular shapes and an uncontrolled vesicle size distribution.

The lipid solution (A) comprises phospholipids. The lipid solution may further contain other lipophilic compounds like for example trans-membrane proteins, peripheral membrane proteins, peptides amphiphiles, ionic polymers, sugar molecules, enzymes and pharmaceutical components and glycolipids. A mixture of lipids can be used. Preferably the amount of phospholipids is at least 97 mol %, relative to the amount of phospholipids and lipophilic compounds.

In general, phospholipids comprise of a headgroup and one or more fatty acid tails. Examples of phospholipid headgroups include Phosphatidylcholine, Phosphatidic acid, Phosphatidylglycerol, Phosphatidylethanolamine and Phosphatidylserine. The fatty acid tail composition can vary in carbon chain length from 12 to 22 carbon atoms and can vary in degree of saturation wherein the C=C double bond can give either cis or trans isomers. Examples of saturated fatty acid tails include lauric acid, myristic acid, palmitic acid, stearic acid and behenic acid. Examples of unsaturated fatty acid tails include myristoleic acid, palmitoleic acid and oleic acid. Variations in fatty acid tail composition are jointly referred to as derivatives of a specific phospholipid headgroup.

Therefore examples of phospholipids include Phosphatidylcholine derivatives, Phosphatidic acid derivatives, Phosphatidylglycerol derivatives, Phosphatidylethanolamine derivatives, Phosphatidylserine derivatives, Natural phospholipid derivatives, polyglycerin-phospholipids, functionalized-phospholipids, terminal activated-phospholipids, and PEGylated phospholipids.

Examples of Phosphatidylcholine derivatives are 1,2-Didecanoyl-sn-glycero-3-phosphocholine (DDPC), 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC), 1,2-Dioleoyl-sn-glycero-3-phosphocholine (DOPC), 1-Palmitoyl-2-oleoyl-sn-glycero-3-phosphocholine (POPC), 1,2-Dierucoyl-sn-glycero-3-phosphocholine (DEPC), DiynePC lipids such as 1,2-bis(10,12-tricosadiynoyl)-sn-glycero-3-phosphocholine and 1-palmitoyl-2-(10,12-tricosadiynoyl)-sn-glycero-3-phosphocholine;

Examples of Phosphatidic acid derivatives are 1,2-dimyristoyl-sn-glycero-3-phosphate (DMPA), 1,2-dipalmitoyl-sn-glycero-3-phosphate (DPPA), 1,2-distearoyl-sn-glycero-3-phosphate (DSPA).

Examples of Phosphatidylglycerol derivatives are 1,2-dimyristoyl-sn-glycero-3[Phospho-rac-(1-glycerol) (DMPG), 1,2-dipalmitoyl-sn-glycero-3[Phospho-rac-(1-glycerol) (DPPG), 1,2-distearoyl-sn-glycero-3[Phospho-rac-(1-glycerol) (DSPG), 1-almitoyl-2-oleoyl-sn-glycero-3[Phospho-rac-(1-glycerol)] (POPG).

Examples of Phosphatidylethanolamine derivatives are 1,2-dimyristoyl-sn-glycero-3-phosphoethanolamine (DMPE), 1,2-dipalmitoyl-sn-glycero-3-phosphoethanolamine (DPPE), 1,2-distearoyl-sn-glycero-3-phosphoethanolamine (DSPE), 1,2-dioleoyl-sn-glycero-3-phosphoethanolamine (DOPE), DiynePE lipids such as 1,2-bis(10,12-tricosadiynoyl)-sn-glycero-3-phosphoethanolamine and 1-palmitoyl-2-(10,12-tricosadiynoyl)-sn-g lycero-3-phosphoethanolamine and conjugated phosphoethanolamines conjugated with, not limited to, peptides, proteins and fluorophores such as Texas Red-1,2-dihexadecanoyl-sn-Glycero-3-Phosphoethanolamine (TR-DHPE).

An example of Phosphatidylserine derivatives is 1,2-dioleoyl-sn-glycero-3-phosphoserine (DOPS).

Examples of PEGylated phospholipids are saturated and unsaturated (e.g. 14:0, 16:0, 18:0 and 18:1) phosphatidylethanolamine derivatives conjugated to polyethylene glycol (PEG). The PEG group in the PEGylated phospholipids have preferably a MW of 200-10,000. PEGylated phospholipids can be chosen from the group consisting of 1,2-distearoyl-sn-glycero-3-phosphoethanolamine-N-[methoxy(polyethylene glycol)-350] (DSPE-PEG350), 1,2-distearoyl-sn-glycero-3-phosphoethanolamine-N-[methoxy(polyethylene glycol)-550] (DSPE-PEG550), 1,2-distearoyl-sn-glycero-3-phosphoethanolamine-N-[methoxy(polyethylene glycol)-750] (DSPE-PEG750), 1,2-distearoyl-sn-glycero-3-phosphoethanolamine-N-[methoxy(polyethylene glycol)-1000] (DSPE-PEG1000), 1,2-distearoyl-sn-glycero-3-phosphoethanolamine-N-[methoxy(polyethylene glycol)-2000] (DSPE-PEG2000), 1,2-distearoyl-sn-g lycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), 1,2-dioleoyl-sn-glycero-3-phosphoethanolamine-N-[methoxy(polyethylene glycol)-350] (DSPE-PEG350), 1,2-dioleoyl-sn-glycero-3-phosphoethanolamine-N-[methoxy(polyethylene glycol)-550] (DSPE-PEG550), 1,2-dioleoyl-sn-glycero-3-phosphoethanolamine-N-[methoxy(polyethylene glycol)-750] (DSPE-PEG750), 1,2-dioleoyl-sn-glycero-3-phosphoethanolamine-N-[methoxy(polyethylene glycol)-1000] (DSPE-PEG1000), 1,2-dioleoyl-sn-glycero-3-phosphoethanolamine-N-[methoxy(polyethylene glycol)-2000] (DSPE-PEG2000), 1,2-dioleoyl-sn-glycero-3-phosphoethanolamine-N-[methoxy(polyethylene glycol)-3000] (DSPE-PEG3000), 1,2-dioleoyl-sn-glycero-3-phosphoethanolamine-N-[methoxy(polyethylene glycol)-5000] (DSPE-PEG5000), 1,2-dipalmitoyl-sn-glycero-3-phosphoethanolamine-N-[methoxy(polyethylene glycol)-350] (DSPE-PEG350), 1,2-dipalmitoyl-sn-glycero-3-phosphoethanolamine-N-[methoxy(polyethylene glycol)-550] (DSPE-PEG550), 1,2-dipalmitoyl-sn-glycero-3-phosphoethanolamine-N-[methoxy(polyethylene glycol)-750] (DSPE-PEG750), 1,2-dipalmitoyl-sn-glycero-3-phosphoethanolamine-N-[methoxy(polyethylene glycol)-1000] (DSPE-PEG1000), 1,2-dipalmitoyl-sn-glycero-3-phosphoethanolamine-N-[methoxy(polyethylene glycol)-2000] (DSPE-PEG2000), 1,2-dioleoyl-sn-glycero-3-phosphoethanolamine-N-[methoxy(polyethylene glycol)-3000] (DSPE-PEG3000) and 1,2-dioleoyl-sn-glycero-3-phosphoethanolamine-N-[methoxy(polyethylene glycol)-5000] (DSPE-PEG5000).

Preferred phospholipids are chosen from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1-palmitoyl-2-oleoyl-sn-glycero-3-phosphocholine (POPC), for example mPEG-phospholipids such as 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000), 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

More preferably the phospholipids are chosen from the group consisting of 1,2-dipalmitoyl-sn-glycero-3-phosphocholine (DPPC), 1,2-dioleoyl-sn-glycero-3-phosphocholine (DOPC), 1,2-dioleoyl-sn-glycero-3-phosphoethanolamine-N-[methoxy(polyethylene glycol)-2000] (DSPE-PEG2000), 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

In general, phospholipids have a hydrophilic head and two hydrophobic tails each. When phospholipids are exposed to water, they arrange themselves into e.g. a two-layered sheet (a bilayer) with all of their tails pointing towards the center of the sheet or as micelles with their tails pointing towards each other. The centers of this bilayer and micelle, contain almost no water and excludes polar molecules that dissolve in water but e.g. not in oil.

At a given temperature a phospholipid bilayer can exist in either a liquid or a gel (solid) phase. All lipids have a characteristic temperature at which they transition (melt) from the gel to the liquid phase—the phase transition temperature. In both phases the phospholipid molecules are mostly prevented from flip-flopping across the bilayer, but in liquid phase bilayers a given lipid will exchange locations with its neighbor millions of times a second. Unlike liquid phase bilayers, the phospholipids in a gel phase bilayer are locked in place with very limited mobility.

While phospholipid tails primarily modulate bilayer phase behavior, it is the head group of the lipid that determines the bilayer surface chemistry. Of the phospholipids, the most common head group is phosphatidylcholine (PC). Phosphatidylcholine is a zwitterionic head group, as it has a negative charge on the phosphate group and a positive charge on the choline but, because these local charges balance, no net charge is present at physiological pH. Another example of a head group with no net charge at physiological pH is phosphatidylethanolamine. Other head groups, such as, phosphatidic acid, phosphatidylserine and phosphatididylglycerol carry a negative charge at physiological pH.

Due to their zwitterionic nature, phosphatidylcholine derivatives are preferably used for coating applications; phosphatidylcholine derivatives are a class of lipids that bear a phosphatidylcholine headgroup and can have natural or synthetic hydrophobic tails of varying length and composition such as degree of saturation. Examples of natural hydrophobic tails are palmitoyl, oleoyl, diphytanoyl, and myristoyl. Examples of synthetic hydrophobic tails are diacetylenic, and acrylate containing tails. Preferably the lipid solution (A) comprises phospholipid derivatives that yield fusogenic (the ability to fuse to the surface of a substrate) lipid vesicles that readily form a lipid-based coating on the substrate. Typically, fusogenic vesicles can be prepared from a preferred group of lipids, namely the phosphatidylcholine derivatives.

Aqueous solution (B) comprises water and optionally salts (e.g. NaCl and $CaCl_2$), buffers, complexing agents and/or water-soluble pharmaceutical components.

Examples of suitable aqueous solutions are milliQ water, demineralized water, phosphate buffered saline (PBS), HEPES buffer, saline solution.

The pH of the aqueous solution (B) ranges between 4 and 9, preferably between 5 and 8. Outside of this pH range (below pH 4 and above pH 9) lipid vesicles with the desired particle size and distribution are not easily formed and the following coating process is not optimal.

The temperature of the aqueous solution (B) should be higher than 0° C. and also exceed the lowest phase transition temperature of phospholipids in solution (A). The temperature of the aqueous solution (B) is generally between 0 and 60° C., preferably between 10 and 50° C., most preferably between 15 and 30° C.

In step III, the aqueous solution (B) is agitated, while the solution (A) is dispensed into the agitated solution (B). The skilled man will realize that different ways of agitation and dispensing can be applied, as long as the water miscible solvent in solution (A) can quickly dissolve in solution (B) so as to make an aqueous dispersion comprising lipid vesicles (C) having a number average size between 40 and 140 nm that can be used to form a lipid-based coating on a substrate.

The agitation of the aqueous solution (B) assists in the quick dispersion of the lipid solution (A) and the fast dissolution of the water miscible solvent in the water, thereby forming nanoparticles comprising lipids (aqueous dispersion comprising lipid vesicles (C)). The mixing process should be carried out in such a way, that the lipids can form lipid vesicles having a number average size between 80 and 120 nm, measured according to dynamic light scattering. At too high concentration of lipid solution (A), too low mixing speed, too low dilution factor of lipid solution (A) in aqueous solution (B), agglomeration of lipid particles can occur leading to irregular shaped particles, particles having a broad size distribution and the like. Formation of irregular and large particles can also be observed by a non-transparent solution, which scatters light and has a milky appearance. When small particles are being formed, with a number average size between 40-140 nm, preferably 80-120 nm, the resulting dispersion is transparent. Transparency can be qualitatively assessed by the skilled man by eye or quantitatively by absorbance measurements at a wavelength of 600 nm (OD600, optical density).

An example of efficiently agitating solution (B) and dispensing solution (A) into solution (B) can be performed by using a stirring plate or vortex and a fluidic device that dispenses solution (A) into (B), respectively. An example of agitating solution (B) is stirring a volume of 25-1000 ml using a Teflon coated stirrer bar and a magnetic stirring plate at 100 to 600 rpm. Agitation of aqueous solution (B) should first reach is steady-state before dispensing solution (A). An example of a suitable fluidic device is an air-displacement micropipette of the kinds P10, P100, P200 and P1000 wherein the volume of solution (A) is dispensed in 0.1-1 second. Preferably a clear dispersion (C) is being obtained with virtually no particles visible to the human eye.

Typically dispensing is performed by introducing solution (A) in solution (B) at 1-10 ml per second, with a dispensing system having a nozzle with an internal diameter between 0.1 and 2 mm, into solution (B).

Solution (A) is being diluted in solution (B) when dispensed into solution (B).

The dilution factor of lipid solution (A) in aqueous solution (B) can range between 100 and 2000, depending on the type of process used, the concentration of lipid solution (A) and the type of aqueous solution. The dilution factor is calculated by dividing the total volume of aqueous solution (B) (before mixing with solution (A)) by the volume of lipid solution (A) to be dosed into the aqueous solution (B). In simple batch operation, the dilution factor is preferably between 500 and 2000, or between 750 and 1500. In continuous operation, like for example in microfluidic devices, the dilution factor may be lower, for example between 100 and 1000, or between 250 and 800.

At these dilution factors, the desired lipid vesicles are obtained which can easily fuse on to the substrate. High dilution factors at any given lipid concentration in solution (A) result in lower amounts of water miscible solvent and lipid vesicles in dispersion (C). The ability to fuse can depend on the amount of lipid vesicles (lipid concentration) in dispersion (C) but also depend on the aqueous solution (B) used. In case the aqueous solution (B) contains merely milliQ water, the lipid concentration in dispersion (C) is typically higher compared to aqueous solution (B) containing salts such as $CalCl_2$. Typically, the phospholipid concentration in dispersion (C) is between 0.05 and 2.0 mg/ml. More preferably, the phospholipid concentration in dispersion (C) is between 0.1 and 1.0 mg/ml.

The temperature during preparation of aqueous dispersion (C) by agitating solution (B) and dispensing solution (A) into solution (B) should be higher than 0° C. and also exceed the lowest phase transition temperature of phospholipids in solution (A). The temperature of is generally between 0 and 60° C., preferably between 10 and 50° C., most preferably between 15 and 30° C.

The aqueous dispersion (C) is prepared as a result of dispensing of solution (A) into agitated solution (B). Typically, the time to prepare dispersion (C) is between 1 and 60 sec. After dispersion (C) is prepared, agitating can be stopped.

The aqueous dispersion (C) contains at least 95 wt. % water, more preferably at least 98 wt. % water. The aqueous dispersion (C) also contains solvent from dispensing solution (A), preferably an alcohol, most preferably ethanol.

The amount of solvent from dispensing solution (A) preferably ranges between 0.05 vol % and 1 vol %, preferably between 0.1 vol % and 0.5 vol %, relative to aqueous dispersion (C).

The aqueous dispersion (C) can be applied to a substrate.

In principle any substrate can be used, as long as the lipid vesicles in dispersion (C) can form a lipid-based coating on the substrate. The substrate can be a material and an object of any size and form. The substrate can be glass, plastic, metal and the like. Glass and polycaprolactone for example can be coated without special pretreatment, while some plastics may need some pretreatment like for example plasma treatment, UV-ozone treatment, the formation of a self-assembled monolayer or further chemical derivatization as described in e.g. US2008/0241942 and WO2014/184383. The aqueous dispersion (C) can be applied to a substrate present in aqueous solution (B) resulting in instant fusion of lipid vesicles into a lipid-based coating on the substrate. Alternatively, the resulting aqueous dispersion (C) can be brought into contact with a substrate, diluted or non-diluted, resulting in the instant fusion of vesicles into a lipid-based coating on the substrate.

The invention also relates to aqueous dispersion (C) comprising phospholipids as defined above, wherein the phospholipids are present as vesicles having a number average size between 40 and 140 nm (measured according to dynamic light scattering), and wherein the phospholipid concentration ranges between 0.05 and 2.0 mg/ml and wherein the dispersion contains at least 95 wt. % of water.

The phospholipids are preferably chosen from Phosphatidylcholine derivatives, Phosphatidic acid derivatives, Phosphatidylglycerol derivatives, Phosphatidylethanolamine derivatives, Phosphatidylserine derivatives, Natural phospholipid derivatives, Sterols, cholesterol, desmosterol, lanosterol and derivatives of sterols, polyglycerin-phospholipids, functionalized-phospholipids, terminal activated-phospholipids, N-[1-(2,3-Dioleoyloxy)propyl]-N,N,N-trimethylammonium methyl-sulfate (DOTAP), PEGylated phospholipids, proteins, peptides, amphiphiles, ionic polymers, sugar molecules, enzymes and pharmaceutical components.

Preferably, the aqueous dispersion (C) containing phospholipid vesicles comprise phosphatidylcholine derivatives and PEGylated phospholipids. More preferably, dispersion (C) contains lipid vesicles comprising of 90-95 mol % (of total phospholipid content) 1,2-dioleoyl-sn-glycero-3-phosphocholine (DOPC) or 1,2-dipalmitoyl-sn-glycero-3-phosphocholine (DPPC) and 5-10 mol % (of total phospholipid content) PEGylated phospholipids such as 1,2-dipalmitoyl-sn-glycero-3-phosphoethanolamine-N-[methoxy(polyethylene glycol)-2000] (DPPE-PEG2000) or 1,2-dioleoyl-sn-glycero-3-phosphoethanolamine-N-[methoxy(polyethylene glycol)-2000] (DOPE-PEG2000) and optionally between 0 and 5 mol % (relative to the total phospholipid content) of additives chosen from fluorescent conjugates, proteins, peptides, amphiphiles, ethylene glycol, polyethylene glycol (PEG), ionic polymers, sugar molecules, enzymes and pharmaceutical components.

The invention also relates to a method for preparing lipid-based coatings on devices, not limited to, medical devices such as contact lenses and catheters, coating of R&D tools such as (micro)fluidic devices and cell culture devices, food production devices, pharma devices and so forth.

The invention also relates to the use of the aqueous dispersion (C) for preparing lipid based coatings on medical devices, such as contact lenses, catheters, (micro)fluidic devices, cell culture devices, food production devices, pharma devices and the like.

The invention further relates to the medical devices having a lipid-based coating as defined above and/or made according to the method of the present invention.

Experiment 1 (Comparative)

Experiment 1 was performed to demonstrate a too high dilution factor of solution (A) in aqueous solution (B) that does not yield a lipid-based coating. To examine a too high dilution factor, solution (A) was prepared at 50 mg/ml using 99.8 mol % of total lipid content of DOPC (Avanti polar lipids) and 0.2 mol % of total lipid content of TR-DHPE (Thermo Fisher) in ethanol (ethanol absolute≥99.8%, VWR). Solution (A) was stored under argon in microcentrifuge containers (VWR) at −20° C. for a maximum of 6 weeks. All lipids were ordered as powdered stocks and kept under argon atmosphere and stored at −20° C. for a maximum of 1 year. Aqueous solution (B) comprised 0.1 M PBS buffer at pH 7.4 (Sigma-Aldrich). In 1.5 mL of aqueous solution (B) at room temperature, 0.75 µL of solution (A) was added thereby using a 2000× dilution factor to 0.025 mg phospholipids per ml. Dispensing of solution (A) into aqueous solution (B) was performed using an air-displacement P10 micropipette (Eppendorf). Agitation was performed using a table-top vortex (labdancer, VWR). Aqueous solution (B) was vortex until steady-state at which point solution (A) was dispensed in 1 second. The resulting aqueous dispersion (C) was characterized using dynamic light scattering (DLS, Nanotrac wave, Microtrac). The mean number-weighted diameter (Mn) was 90.8±29.6 nm and the solution appeared transparent by visual observation. 100 µL of dispersion (C) was added per well of a 96-well glass bottoms plates (SensoPlates, Greiner Bio-one). The 96-well glass bottoms plates were cleaned beforehand by incubation of 300 µL 2 v/v % Hellmanex III (Sigma-Aldrich) solution in milliQ for 1 hour at room temperature and subsequently rinsed with demi water to remove the detergent. Aqueous dispersion (C) was left to incubate for at least 5 minutes to form a lipid-based coating and subsequently washed with milliQ by means of serial dilution through addition of 100 µL of milliQ and removal of 100 µL of solution. At least 16 serial dilution were performed to remove remnants of aqueous dispersion (C). The glass wells were characterized using fluorescence microscopy. To this end, an Olympus inverted IX71 epi-fluorescence research microscope with a Xenon X-cite 120PC as light source and a digital Olympus DR70 camera for image acquisition was used to acquire fluorescence micrographs. TR-DHPE was imaged using $510 \leq \lambda_{ex} \leq 50$ nm and $\lambda_{em} > 590$ nm. Fluorescent Recovery After Photobleaching (FRAP) experiments were performed. FRAP was performed using a confocal microscope (Nikon confocal A1) was used to deduce the signature mobility or immobility of the lipid coating as indicated by the lateral diffusion coefficient, D. Image analysis was performed using ImageJ (NIH), Origin (OriginLab) and Excel (Microsoft). The diffusion coefficient was deduced using modified Bessel functions as described by Soumpasis et al. 1983. Data was corrected for bleaching during image acquisition and normalized and processed with FRAPAnalyser (University of Luxembourg).

Although aqueous dispersion (C) contained lipid vesicles of the correct size, as indicated by DLS, after fluorescence examination of the glass surface no lipid-based coating was found. The concentration of lipid material was insufficient to form a lipid-based coating on the glass substrate.

Experiment 2

Experiment 2 was performed to demonstrate an applicable dilution factor of solution (A) in aqueous solution (B) and an applicable phospholipid concentration in aqueous dispersion (C).

Solution (A), aqueous solution (B) and the glass substrate were prepared as described in Experiment 1. The process of preparing aqueous dispersion (C), applying aqueous dispersion (C) to the glass substrate and its characterization was performed as described in Experiment 1, with the exception of using the following dilution factor; 1000× [0.05 mg phospholipids per ml in aqueous dispersion (C)]. DLS characterization revealed that the desired lipid vesicles were present in aqueous dispersion (C) with Mn of 93.6±35.7 nm. The aqueous dispersion (C) was transparent by means of visual inspection. In addition, lipid-based coating formation was observed on the glass substrate as indicated by the fluorescence and the expected lateral mobility (D) deduced using FRAP.

Experiment 3

Experiment 3 was performed to demonstrate an applicable dilution factor of solution (A) in aqueous solution (B) and an applicable phospholipid concentration in aqueous dispersion (C).

Solution (A), aqueous solution (B) and the glass substrate were prepared as described in Experiment 1. The process of preparing aqueous dispersion (C), applying aqueous dispersion (C) to the glass substrate and its characterization was performed as described in Experiment 1, with the exception of using the following dilution factor; 500× [0.10 mg phospholipids per ml in aqueous dispersion (C)]. DLS characterization revealed that the desired lipid vesicles were present in aqueous dispersion (C) with Mn of 93.0±29.6 nm for experiment 3. The aqueous dispersion (C) was transparent by means of visual inspection. In addition, lipid-based coating formation was observed on the glass substrate as indicated by the fluorescence and the expected lateral mobility (D) deduced using FRAP.

Experiment 4

Experiment 4 was performed to demonstrate an applicable dilution factor of solution (A) in aqueous solution (B) and an applicable phospholipid concentration in aqueous dispersion (C).

Solution (A), aqueous solution (B) and the glass substrate were prepared as described in Experiment 1. The process of preparing aqueous dispersion (C), applying aqueous dispersion (C) to the glass substrate and its characterization was performed as described in Experiment 1, with the exception of using the following dilution factor; 200× [0.25 mg phospholipids per ml in aqueous dispersion (C)]. DLS characterization revealed that the desired lipid vesicles were present in aqueous dispersion (C) with Mn of 87.3±37.4 nm for experiment 4. The aqueous dispersion (C) was transparent by means of visual inspection. In addition, lipid-based coating formation was observed on the glass substrate as indicated by the fluorescence and the expected lateral mobility (D) deduced using FRAP.

Experiment 5

Experiment 5 was performed to demonstrate an applicable dilution factor of solution (A) in aqueous solution (B) and an applicable phospholipid concentration in aqueous dispersion (C).

Solution (A), aqueous solution (B) and the glass substrate were prepared as described in Experiment 1. The process of preparing aqueous dispersion (C), applying aqueous dispersion (C) to the glass substrate and its characterization was performed as described in Experiment 1, with the exception of using the following dilution factor; 100× [0.50 mg phospholipids per ml in aqueous dispersion (C)]. DLS characterization revealed that the desired lipid vesicles were present in aqueous dispersion (C) with Mn of 88.5±31.5 nm for experiment 5. The aqueous dispersion (C) was transparent by means of visual inspection. In addition, lipid-based coating formation was observed on the glass substrate as indicated by the fluorescence and the expected lateral mobility (D) deduced using FRAP.

Experiment 6 (Comparative)

Experiment 6 was performed to demonstrate a too low dilution factor of solution (A) in aqueous solution (B) that does not yield a lipid-based coating. Solution (A) and the glass substrate were prepared as described in Example 1. Aqueous solution (B) comprised of HEPES buffer at pH 7.4 (Sigma-Aldrich) containing 150 mM NaCl (Sigma-Aldrich) and 2 mM $CaCl_2$ pH (Sigma-Aldrich). The process of preparing aqueous dispersion (C), applying aqueous dispersion (C) to the glass substrate and its characterization was performed as described in Example 1, with the exception of using to 50× dilution factor resulting in 1.00 mg phospholipids per ml in aqueous dispersion (C). DLS characterization revealed that lipid vesicles were present in aqueous dispersion (C) having a Mn of 55.5±16.2 nm. The measured size distribution was outside of the desired range of Mn 80 to Mn 120 nm. In addition, the aqueous dispersion (C) appeared less transparent compared to Experiments 2-5. As a result, no lipid-based coating formation was observed on the glass substrate as indicated by the absence fluorescence. Most likely, a too high concentration of ethanol was present in aqueous dispersion (C) due to the too low dilution factor.

Experiment 7 (Comparative)

Experiment 7 was performed to demonstrate a too high concentration of phospholipids in solution (A) that does not yield a lipid-based coating. Solution (A) was prepared at 500 mg/ml using 99.8 mol % of total lipid content of DOPC (Avanti polar lipids) and 0.2 mol % of total lipid content of TR-DHPE (Thermo Fisher) in ethanol (ethanol absolute≥99.8%, R). Aqueous solution (B) comprised of 0.01 M HEPES buffer at pH 7.4 (Sigma-Aldrich) containing 150 mM NaCl (Sigma-Aldrich) and 2 mM $CaCl_2$ pH (Sigma-Aldrich). The glass substrate was prepared as described in Experiment 1. The process of preparing aqueous dispersion (C), applying aqueous dispersion (C) to the glass substrate and its characterization was performed as described in Experiment 1, with the exception of using the following dilution factor; 10000× [0.05 mg phospholipids per ml in aqueous dispersion (C)]. DLS characterization revealed that the desired lipid vesicles were not present in aqueous dispersion (C) and no reliable Mn could be deduced for experiment 7. As a result, no lipid-based coating formation was observed on the glass substrate as indicated by the absence fluorescence. Most likely, the too high concentration of phospholipids was present in solution (A) that prevented adequate dissolution of the water-miscible solvent and formation of desired lipid vesicles.

Experiment 8 (Comparative)

Experiment 8 was performed to demonstrate a too high concentration of phospholipids in solution (A) that does not yield a lipid-based coating. Solution (A) was prepared at 500 mg/ml using 99.8 mol % of total lipid content of DOPC (Avanti polar lipids) and 0.2 mol % of total lipid content of TR-DHPE (Thermo Fisher) in ethanol (ethanol absolute≥99.8%, VWR). Aqueous solution (B) comprised of 0.01 M HEPES buffer at pH 7.4 (Sigma-Aldrich) containing 150 mM NaCl (Sigma-Aldrich) and 2 mM $CaCl_2$ pH (Sigma-Aldrich). The glass substrate was prepared as described in Experiment 1. The process of preparing aqueous dispersion (C), applying aqueous dispersion (C) to the glass substrate and its characterization was performed as described in Experiment 1, with the exception of using the following dilution factor; 5000× [0.10 mg phospholipids per ml in aqueous dispersion (C)]. DLS characterization revealed that the desired lipid vesicles were not present in aqueous dispersion (C) and no reliable Mn could be deduced for experiment 8. As a result, no lipid-based coating formation was observed on the glass substrate as indicated by the absence fluorescence. Most likely, the too high concentration of phospholipids was present in solution (A) that prevented adequate dissolution of the water-miscible solvent and formation of desired lipid vesicles.

Experiment 9

Experiment 9 was performed to demonstrate the applicability of the invention on medical devices. Solution (A) and aqueous solution (B) were prepared as described in Experiment 3. The substrates were contact lens medical devices. More specifically, the substrates were RGP contact lenses comprising of Menicon EX material. The contact lens substrates were cleaned by rinsing with ethanol (ethanol absolute≥99.8%, VWR) and subsequent rinsing with milliQ. The contact lens substrates were dried with $N_2$ gas and treated for 60 s with oxygen plasma at 200 mtorr at 40 watts (Plasma prep II, SPI supplies). The process of preparing aqueous dispersion (C) was performed as described phospholipids per ml in aqueous dispersion (C). Immediately after plasma treatment, the contact lenses were placed in a placed 24 wells plate (Greiner Bio-one) to which 1 mL of dispersion (C) was added. Aqueous dispersion (C) was left to incubate for at least 5 minutes to form a lipid-based coating and subsequently washed with milliQ by means of serial dilution through addition of 1000 µL of milliQ and removal of 1000 µL of solution. At least 16 serial dilution were performed to remove remnants of aqueous dispersion (C). Characterization of the contact lenses was performed as described in Experiment 1. DLS characterization revealed that the desired lipid vesicles were present in aqueous dispersion (C) with a Mn of 107.7±44.2 nm. The aqueous dispersion (C) was transparent by means of visual inspection. In addition, lipid-based coating formation on contact lens medical devices was observed as indicated by the fluorescence and the expected lateral mobility (D) deduced using FRAP.

Experiment 10

Experiment 10 was performed to demonstrate the applicability of the invention on medical devices. Solution (A) and aqueous solution (B) were prepared as described in Experiment 3. The substrates were contact lens medical devices. More specifically, the substrates were RGP contact lenses comprising of Menicon Z material. The contact lens substrates were cleaned by rinsing with ethanol (ethanol absolute≥99.8%, R) and subsequent rinsing with milliQ. The contact lens substrates were dried with $N_2$ gas and treated for 60 s with oxygen plasma at 200 mtorr at 40 watts (Plasma prep II, SPI supplies). The process of preparing aqueous dispersion (C) was performed as described phospholipids per ml in aqueous dispersion (C). Immediately after plasma treatment, the contact lenses were placed in a placed 24 wells plate (Greiner Bio-one) to which 1 mL of dispersion (C) was added. Aqueous dispersion (C) was left to incubate for at least 5 minutes to form a lipid-based coating and subsequently washed with milliQ by means of serial dilution through addition of 1000 µL of milliQ and removal of 1000 µL of solution. At least 16 serial dilution were performed to remove remnants of aqueous dispersion (C). Characterization of the contact lenses was performed as described in Experiment 1. DLS characterization revealed that the desired lipid vesicles were present in aqueous dispersion (C) with a Mn of 107.7±44.2 nm. The aqueous dispersion (C) was transparent by means of visual inspection. In addition, lipid-based coating formation on contact lens medical devices was observed as indicated by the fluorescence and the expected lateral mobility (D) deduced using FRAP.

Experiment 11

Experiments 11 was performed to demonstrate the preparation of PEGylated lipid-based coatings. Solution (A) and aqueous solution (B) were prepared as described in Experiment 6. For experiment 11, solution (A) was prepared at 50 mg/ml using 94.5 mol % of total lipid content of DOPC (Avanti polar lipids), 5 mol % of total lipid content of DOPE-PEG2000 (Avanti polar lipids) and 0.5 mol % of total lipid content of TR-DHPE (Thermo Fisher) in ethanol (ethanol absolute≥99.8%, R). Solution (A) was stored under argon at stored in microcentrifuge containers (VWR) at −20° C. for a maximum of 6 weeks. Aqueous solution (B) were prepared as described in Experiment 3 and the glass substrate were prepared as described in Experiment 1. The process of preparing aqueous dispersion (C), applying aqueous dispersion (C) to the glass substrate and its characterization was performed as described in Experiment 1, with the exception of using a 1000× dilution factor resulting in 0.05 mg of phospholipids per ml in aqueous dispersion (C). DLS characterization revealed that the desired lipid vesicles were present in aqueous dispersion (C) with a Mn of 88.6±1.1 nm for experiment 11. The aqueous dispersion (C) for experiment 11 was transparent by means of visual inspection. In addition, PEGylated lipid-based coating formation on glass substrates was observed as indicated by the fluorescence and the expected lateral mobility (D) deduced using FRAP.

Experiment 12

Experiments 12 was performed to demonstrate the preparation of PEGylated lipid-based coatings. Solution (A) and aqueous solution (B) were prepared as described in Experiment 6. For experiment 12, solution (A) was prepared at 50 mg/ml using 89.5 mol % of total lipid content of DOPC (Avanti polar lipids), 10 mol % of total lipid content of DOPE-PEG2000 (Avanti polar lipids) and 0.5 mol % of total lipid content of TR-DHPE (Thermo Fisher) in ethanol (ethanol absolute≥99.8%, VWR). Solution (A) was stored under argon at stored in microcentrifuge containers (VWR) at −20° C. for a maximum of 6 weeks. Aqueous solution (B) were prepared as described in Experiment 3 and the glass substrate were prepared as described in Experiment 1. The process of preparing aqueous dispersion (C), applying aqueous dispersion (C) to the glass substrate and its characterization was performed as described in Experiment 1, with the exception of using a 1000× dilution factor resulting in 0.05 mg of phospholipids per ml in aqueous dispersion (C). DLS characterization revealed that the desired lipid vesicles were present in aqueous dispersion (C) with a Mn 80.4±3.6 nm for experiment 12. The aqueous dispersions (C) for experiment 12 was transparent by means of visual inspection. In addition, PEGylated lipid-based coating formation on glass substrates was observed as indicated by the fluorescence and the expected lateral mobility (D) deduced using FRAP.

TABLE 1

| | Lipid-1 | Lipid-2 | Lipid-3 | Concentration (A) | Solvent (A) | Aqueous solution (B) | Dilution factor | Aqueous dispersion (C) | Mn (nm)* | Substrate in (C) | Lipid coating formation | wt % water in (C) |
|---|---|---|---|---|---|---|---|---|---|---|---|---|
| exp 1 | 99.8 mol %, DOPC | 0.2 mol %, TR-DHPE | — | 50 mg/mL | Ethanol | PBS | 2000 | 0.025 mg/mL | 90.8 ± 29.6 | Glass | No | 99 |
| exp 2 | 99.8 mol %, DOPC | 0.2 mol %, TR-DHPE | — | 50 mg/mL | Ethanol | PBS | 1000 | 0.05 mg/mL | 93.6 ± 35.7 | Glass | Yes | 99 |
| exp 3 | 99.8 mol %, DOPC | 0.2 mol %, TR-DHPE | — | 50 mg/mL | Ethanol | PBS | 500 | 0.10 mg/mL | 93.0 ± 29.6 | Glass | Yes | 99 |
| exp 4 | 99.8 mol %, DOPC | 0.2 mol %, TR-DHPE | — | 50 mg/mL | Ethanol | PBS | 200 | 0.25 mg/mL | 87.3 ± 37.4 | Glass | Yes | 99 |
| exp 5 | 99.8 mol %, DOPC | 0.2 mol %, TR-DHPE | — | 50 mg/mL | Ethanol | PBS | 100 | 0.50 mg/mL | 88.5 ± 31.5 | Glass | Yes | 99 |
| exp 6 | 99.8 mol %, DOPC | 0.2 mol %, TR-DHPE | — | 50 mg/mL | Ethanol | HEPES | 50 | 1.00 mg/mL | 55.5 ± 16.2 | Glass | No | 98 |
| exp 7 | 99.8 mol %, DOPC | 0.2 mol %, TR-DHPE | — | 500 mg/mL | Ethanol | HEPES | 10000 | 0.05 mg/mL | N.A. | Glass | No | 98 |
| exp 8 | 99.8 mol %, DOPC | 0.2 mol %, TR-DHPE | — | 500 mg/mL | Ethanol | HEPES | 5000 | 0.1 mg/mL | N.A. | Glass | No | 98 |
| exp 9 | 99.8 mol %, DOPC | 0.2 mol %, TR-DHPE | — | 50 mg/mL | Ethanol | HEPES | 100 | 0.1 mg/mL | 107.7 ± 44.2 | Menicon EX | Yes | 98 |
| exp 10 | 99.8 mol %, DOPC | 0.2 mol %, TR-DHPE | — | 50 mg/mL | Ethanol | HEPES | 100 | 0.50 mg/mL | 107.7 ± 44.2 | Menicon Z | Yes | 98 |
| exp 11 | 94.5 mol %, DOPC | 0.5 mol %, TR-DHPE | 5 mol % DOPE-PEG2000 | 50 mg/mL | Ethanol | HEPES | 1000 | 0.05 mg/mL | 88.6 ± 1.1 | Glass | Yes | 98 |
| exp 12 | 89.5 mol %, DOPC | 0.5 mol %, TR-DHPE | 10 mol % DOPE-PEG2000 | 50 mg/mL | Ethanol | HEPES | 1000 | 0.05 mg/mL | 80.4 ± 3.6 | Glass | Yes | 98 |

What is claimed is:

1. A process for making lipid-coated substrates comprising the steps of:
   a. providing a lipid solution (A) of phospholipids in a water miscible organic solvent at a phospholipid concentration between 25 and 450 mg/ml;
   b. providing an aqueous solution (B) having pH between 4 and 8;
   c. agitating the aqueous solution (B) and dispense the lipid solution (A) into the aqueous solution (B) to prepare an aqueous dispersion comprising lipid vesicles (C) having a number average size between 80 and 120 nm (measured according to dynamic light scattering) at a phospholipid concentration between 0.05 mg/ml and 2 mg/ml; and
   d. applying the aqueous dispersion (C) to a substrate and forming of a lipid-based coating;
   wherein aqueous dispersion (C) contains at least 95 wt. % water and,
   wherein the aqueous dispersion contains between 0.1 vol % and 1 vol % of an alcohol.

2. The process according to claim 1, wherein the organic solvent is methanol, ethanol, propanol, acetone, dimethylformamide, glycerol, polyethylene glycol (PEG), or dimethylsulfoxide or any combination thereof.

3. The process according to claim 2, wherein the organic solvent is an alcohol.

4. The process according to claim 3, wherein the organic solvent is ethanol.

5. The process according to claim 1, wherein a temperature of the lipid solution (A) is between −20 and 60° ° C.

6. The process according to 5, wherein the temperature of the lipid solution (A) is between 10 and 50° C.

7. The process according to 6, wherein the temperature of the lipid solution (A) is between 15 and 30° C.

8. The process according to claim 1, wherein the phospholipids are chosen from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), 1-palmitoyl-2-oleoyl-sn-glycero-3-phosphocholine (POPC), and mPEG-phospholipids.

9. The process according to claim 8, wherein the mPEG-phospholipids are one or more of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000), 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

10. The process according to claim 1, wherein the phospholipids are chosen from the group consisting of 1,2-dipalmitoyl-sn-glycero-3-phosphocholine (DPPC) and 1,2-dioleoyl-sn-glycero-3-phosphocholine (DOPC).

11. The process according to claim 1, wherein the phospholipids comprise at least one or more PEGylated phospholipids, wherein the PEGylated phospholipids are chosen from the group consisting of 1,2-distearoyl-sn-glycero-3- phosphoethanolamine-N-[methoxy(polyethylene glycol)-350] (DSPE-PEG350), 1,2-distearoyl-sn-glycero-3-phosphoethanolamine-N-[methoxy(polyethylene glycol)-550] (DSPE-PEG550), 1,2-distearoyl-sn-glycero-3-phosphoethanolamine-N-[methoxy(polyethylene glycol)-750] (DSPE-PEG750), 1,2-distearoyl-sn-glycero-3-phosphoethanolamine-N-[methoxy(polyethylene glycol)-1000] (DSPE-PEG1000), 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[methoxy(polyethylene glycol)-3000] (DSPE-PEG3000), 1,2-distearoyl-sn-glycero-3-phosphoethanolamine-N-[methoxy(polyethylene glycol)-5000] (DSPE-PEG5000), 1,2-dioleoyl-sn-glycero-3-phosphoethanolamine-N-[methoxy(polyethylene glycol)-350] (DOPE-PEG350), 1,2-dioleoyl-sn-glycero-3-phosphoethanolamine-N-[methoxy(polyethylene glycol)-550] (DOPE-PEG550), 1,2-dioleoyl-sn-glycero-3-phosphoethanolamine-N-[methoxy(polyethylene glycol)-750] (DOPE-PEG750), 1,2-dioleoyl-sn-glycero-3-phosphoethanolamine-N-[methoxy(polyethylene glycol)-1000] (DOPE-PEG1000), 1,2-dioleoyl-sn-glycero-3-phosphoethanolamine-N-[methoxy(polyethylene glycol)-2000] (DOPE-PEG2000), 1,2-dioleoyl-sn-glycero-3-phosphoethanolamine-N-[methoxy(polyethylene glycol)-3000] (DOPE-PEG3000), 1,2-dioleoyl-sn-glycero-3-phosphoethanolamine-N-[methoxy(polyethylene glycol)-5000] (DOPE-PEG5000), 1,2-dipalmitoyl-sn-glycero-3-phosphoethanolamine-N-[methoxy(polyethylene glycol)-350] (DPPE-PEG350), 1,2-dipalmitoyl-sn-glycero-3-phosphoethanolamine-N-[methoxy(polyethylene glycol)-550] (DPPE-PEG550), 1,2-dipalmitoyl-sn-glycero-3-phosphoethanolamine-N-[methoxy(polyethylene glycol)-750] (DPPE-PEG750), 1,2-dipalmitoyl-sn-glycero-3-phosphoethanolamine-N-[methoxy(polyethylene glycol)-1000] (DPPE-PEG1000), 1,2-dipalmitoyl-sn-glycero-3-phosphoethanolamine-N-[methoxy(polyethylene glycol)-2000] (DPPE-PEG2000), 1,2-dioleoyl-sn-glycero-3-phosphoethanolamine-N-[methoxy(polyethylene glycol)-3000] (DOPE-PEG3000) and 1,2-dioleoyl-sn-glycero-3-phosphoethanolamine-N-[methoxy(polyethylene glycol)-5000] (DOPE-PEG5000).

12. The process according to claim 11, wherein the PEGylated phospholipids are chosen from the group consisting of 1,2-dipalmitoyl-sn-glycero-3-phosphoethanolamine-N-[methoxy(polyethylene glycol)-2000] (DPPE-PEG2000) and 1,2-dioleoyl-sn-glycero-3-phosphoethanolamine-N-[methoxy(polyethylene glycol)-2000] (DOPE-PEG2000).

13. The process according to claim 1, wherein the aqueous solution (B) comprises water and optionally salts, buffers, complexing agents and/or water-soluble active or non-active pharmaceutical components.

14. The process according to claim 13, wherein the salt is present and is one or more of NaCl and $CaCl_2$.

15. The process according to claim 1, wherein the aqueous solution is one or more of milliQ water, demineralized water, phosphate buffered saline (PBS), 2-[4-(2-hydroxyethyl)-piperazin-1-yl]ethane-1-sulfonic acid (HEPES) buffer, and a saline solution.

16. The process according to claim 1, wherein a dilution factor of lipid solution (A) in aqueous solution (B) ranges between 100 and 1000, wherein the dilution factor is calculated by dividing the total volume of aqueous solution (B) (before mixing with solution (A)) by the volume of lipid solution (A) to be dosed into the aqueous solution (B).

17. An aqueous dispersion (C), comprising:
  phospholipids, wherein the phospholipids are present as vesicles having a number average size between 40 and 140 nm (measured according to dynamic light scattering), wherein the phospholipid concentration ranges between 0.05 and 2.0 mg/ml, wherein the dispersion contains at least 95 wt. % of water, wherein the dispersion contains between 0.1 vol % and 1 vol % of an alcohol, and wherein the phospholipids are chosen from Phosphatidylcholine derivatives, Phosphatidic acid derivatives, Phosphatidylglycerol derivatives, Phosphatidylethanolamine derivatives, Phosphatidylserine derivatives, Natural phospholipid derivatives, polyglycerin-phospholipids, terminal activated-phospholipids, and PEGylated phospholipids, wherein derivatives are fatty acids tails having between 12 and 22 C-atoms.

18. The aqueous dispersion (C) according to claim 17, wherein the dispersion contains phospholipid vesicles comprise of phosphatidylcholine derivatives and PEGylated phospholipids.

19. The dispersion according to claim 17, wherein the dispersion (C) contains lipid vesicles comprising of 90-95 mol % (of total phospholipid content) 1,2-dioleoyl-sn-glycero-3-phosphocholine (DOPC) or 1,2-dipalmitoyl-sn-glycero-3-phosphocholine (DPPC) and 5-10 mol % (of total phospholipid content) PEGylated phospholipids and optionally between 0 and 5 mol % (relative to the total phospholipid content) of additives chosen from fluorescent conjugates, proteins, peptides, amphiphiles, ethylene glycol, polyethylene glycol (PEG), ionic polymers, sugar molecules, enzymes and pharmaceutical components.

20. The process according to claim 19, wherein the PEGylated phospholipid are one or more of 1,2-dipalmitoyl-sn-glycero-3-phosphoethanolamine-N-[methoxy(polyethylene glycol)-2000] (DPPE-PEG2000) or 1,2-dioleoyl-sn-glycero-3-phosphoethanolamine-N-[methoxy(polyethylene glycol)-2000] (DOPE-PEG2000).

21. A method, comprising the step of:
  applying the aqueous dispersion (C) according to claim 17 on a medical device, contact lens, catheter, (micro) fluidic device, cell culture device, food production device, or pharma device.

22. An object comprising the lipid-based coating as prepared according to the process of claim 1.

23. A process for making lipid-coated substrates comprising the steps of:
  a. providing a lipid solution (A) of phospholipids in a water miscible organic solvent at a phospholipid concentration between 25 and 450 mg/ml, wherein the water miscible organic solvent is one or more of methanol, ethanol, propanol, acetone, dimethylformamide, glycerol, polyethylene glycol, and dimethylsulfoxide;
  b. providing an aqueous solution (B) having pH between 4 and 8;
  c. agitating the aqueous solution (B) and dispense the lipid solution (A) into the aqueous solution (B) to prepare an aqueous dispersion comprising lipid vesicles (C) having a number average size between 80 and 120 nm (measured according to dynamic light scattering) at a phospholipid concentration between 0.05 mg/ml and 2 mg/ml; and d. applying the aqueous dispersion (C) to a substrate and forming of a lipid-based coating;

wherein aqueous dispersion (C) contains at least 95 wt. % water.

* * * * *